(12) United States Patent
Rivlin et al.

(10) Patent No.: US 12,714,331 B2
(45) Date of Patent: Aug. 25, 2026

(54) 3-DIMENSIONAL AUGMENTED REALITY SCANNER FOR CUSTOMIZED MEDICAL IMMOBILIZATION DEVICES

(71) Applicant: Dimension Orthotics, LLC, Philadelphia, PA (US)

(72) Inventors: Michael Rivlin, Philadelphia, PA (US); Pedro K. Beredjiklian, Philadelphia, PA (US); Ashkan Sedigh, Philadelphia, PA (US); Michael J. Sileski, Philadelphia, PA (US)

(73) Assignee: DIMENSION ORTHOTICS, LLC, Philadelphia, PA (US)

( * ) Notice: Subject to any disclaimer, the term of this patent is extended or adjusted under 35 U.S.C. 154(b) by 79 days.

(21) Appl. No.: 18/955,056

(22) Filed: Nov. 21, 2024

(65) Prior Publication Data

US 2025/0160681 A1 May 22, 2025

Related U.S. Application Data

(60) Provisional application No. 63/601,662, filed on Nov. 21, 2023.

(51) Int. Cl.
*A61B 5/107* (2006.01)
*A61B 5/00* (2006.01)
(Continued)

(52) U.S. Cl.
CPC .......... *A61B 5/1079* (2013.01); *A61B 5/0064* (2013.01); *A61B 5/0079* (2013.01);
(Continued)

(58) Field of Classification Search
CPC ... A61B 5/1079; A61B 5/0064; A61B 5/0079; A61B 5/1077; A61B 5/7264;
(Continued)

(56) References Cited

U.S. PATENT DOCUMENTS 4,161,175 A 7/1979 Bentele
5,556,373 A 9/1996 Motloch
(Continued)

FOREIGN PATENT DOCUMENTS

CN 204461463 U 7/2015
CN 104266587 B 4/2017
DE 102011119658 B4 4/2014

OTHER PUBLICATIONS

SureScan 3D app, iPhone 3D scanner, iPad 3D Scanner: Xyken LLC. Xyken. (Dec. 8, 2022). https://web.archive.org/web/20221208224453/https:/www.xyken.com/surescan-3d-app. (Year: 2022).*

(Continued)

*Primary Examiner* — Peter H Choi
*Assistant Examiner* — Sara Jessica Morice De Vargas
(74) *Attorney, Agent, or Firm* — Panitch Schwarze Belisario & Nadel LLP

(57) ABSTRACT

A system for 3D scanning and visualization for modelling an orthotic including a scanning device having a LiDAR and a TrueDepth camera that is configured as a sensor configured to capture depth information from objects, available in either LiDAR or TrueDepth camera configurations, and a laser-assisted device to configure resolution. The system including augmented reality or virtual reality glasses, a charging console, a software interface and a handheld station to cover the sensor. The virtual reality glasses configured to overlay digital information onto real world objects. The charging console comprised of a station configured to provide power and replenish a battery. The software interface configured to process, analyze, and display data captured by the scanning device and interact with the virtual reality glasses. The handheld station configured to cover the sensor, accessories,
(Continued)

and laser-assisted device that is connected to the virtual reality glasses.

23 Claims, 4 Drawing Sheets

(51) Int. Cl.
*A61F 5/01* (2006.01)
*G16H 80/00* (2018.01)
*A61B 90/00* (2016.01)
*A61B 90/50* (2016.01)

(52) U.S. Cl.
CPC .......... *A61B 5/1077* (2013.01); *A61B 5/7264* (2013.01); *A61B 5/7465* (2013.01); *A61F 5/01* (2013.01); *G16H 80/00* (2018.01); *A61B 2090/365* (2016.02); *A61B 2090/502* (2016.02); *A61B 2560/0456* (2013.01)

(58) Field of Classification Search
CPC ............ A61B 5/7465; A61B 2090/365; A61B 2090/502; A61B 2560/0456; A61B 5/055; A61B 5/447; A61B 5/486; A61B 5/6844; A61B 5/7267; A61B 5/6887; A61B 5/745; A61F 5/01; G16H 80/00
USPC ........................................................... 705/2
See application file for complete search history.

(56) References Cited

U.S. PATENT DOCUMENTS

| | | | | |
|---|---|---|---|---|
| 5,870,220 | A | 2/1999 | Migdal et al. | |
| 6,725,118 | B1 | 4/2004 | Fried et al. | |
| 9,855,115 | B2 | 1/2018 | Tam et al. | |
| 10,535,203 | B2 | 1/2020 | Huang et al. | |
| 10,716,525 | B2 | 7/2020 | Weingarten et al. | |
| 10,758,396 | B2 | 9/2020 | Rivlin et al. | |
| 2002/0028418 | A1 | 3/2002 | Farag et al. | |
| 2005/0015172 | A1 | 1/2005 | Fried et al. | |
| 2005/0080369 | A1 | 4/2005 | Kim | |
| 2007/0223009 | A1 | 9/2007 | Erfling et al. | |
| 2010/0087803 | A1 | 4/2010 | Rastegar et al. | |
| 2010/0138193 | A1 | 6/2010 | Summit et al. | |
| 2011/0301520 | A1 | 12/2011 | Summit et al. | |
| 2016/0074203 | A1 | 3/2016 | Hall | |
| 2017/0104925 | A1 | 4/2017 | Ng et al. | |
| 2017/0311896 | A1 | 11/2017 | Morger | |
| 2018/0028108 | A1 | 2/2018 | Shluzas et al. | |
| 2018/0144547 | A1 | 5/2018 | Shakib et al. | |
| 2018/0321374 | A1 | 11/2018 | Qi et al. | |
| 2019/0247165 | A1 | 8/2019 | Müllner et al. | |
| 2020/0275995 | A1 | 9/2020 | Bühler et al. | |
| 2020/0323496 | A1 * | 10/2020 | Eibenberger | A61B 5/746 |
| 2022/0211533 | A1 * | 7/2022 | Johnson | A61F 5/0125 |
| 2022/0313402 | A1 * | 10/2022 | Katzman | A61C 7/002 |

OTHER PUBLICATIONS

Avsar, E., & Un, K. (Apr. 25, 2016). Automatic 3D modeling and simulation of bone-fixator system in a novel graphical user interface. https://doi.org/10.1016/j.imu.2016.04.002 (Year: 2016).*

Lin, M.-H., & Lee, L. (Oct. 13, 2023). Designing the prosthetic appearance in virtual reality with the collaboration of participants and users . https://dl.designresearchsociety.org/cgi/viewcontent.cgi?article=1056&context=iasdr (Year: 2023).*

Hale, L., Linley, E. & Kalaskar, D.M. A digital workflow for design and fabrication of bespoke orthoses using 3D scanning and 3D printing, a patient-based case study. Sci Rep 10, 7028 (2020). https://doi.org/10.1038/s41598-020-63937-1 (Year: 2020).*

Sheehan, F. H., Ricci, M. A., Murtagh, C., Clark, H., & Bolson, E. L. (Feb. 5, 2010). Expert visual guidance of ultrasound for Telemedicine. Journal of telemedicine and telecare. (Year: 2010).*

Tyrrell, J. (Jun. 16, 2023). Lidar in smartphones â business opportunities for 3D scanning. TechHQ. https://techhq.com/news/lidar-in-smartphones-business-opportunities-for-3d-scanning/ (Year: 2023).*

Randall Marsh, 3D-printed Cortex concept scratches the itch of healing broken bones, Jul. 2, 2013.

Nina Golgowski, Revolutionary 3-D printed cast could be the future of comfort and design—New York Daily News, Jul. 14, 2013.

Stoppress Team, New Zealander's 3D printed design could do away with smelly casts forever—Jul. 9, 2013.

ICON Magazine, 2013 Icon Awards winner—Cortex 3D-printed cast, Technology of the Year—Jan. 23, 2014.

Chris Welch, 3D-printed 'Cortex' cast concept puts a modern spin on bone fracture treatment, The Verge, Jun. 29, 2013.

DeZeen, Cortex 3D-printed cast for fractured bones by Jake Evill, Jun. 28, 2013.

Jack Evill, Cortex Exoskeleton Publication, 2013.

Deniz Karasashin, Osteoid Medical Cast, attachable bond stimulator, A Design Award Competition, Osteoid Medical, Sep. 30, 2025.

Active Armor, downloaded from web page: http://activarmor.com/, Download date May 2017, original posting date: unknown, 2 pages.

Xkelet Easy Life, downloaded from web page:https://www.xkelet.com/?lang=en>, 2017, Download date: May 2017, original date: unknown, 8 pages.

MHOX, 2012, downloaded from web page: http://mhoxdesign.com, Download date: May 2017, original posting dtae: unknown, 1 page.

Exovite, 2015, downloaded from web page: exovite.com <http://exovite.com, Download date: May 2017, original posting date: unknown, 2 pages.

3D Printing Industry, The Authority on 3D Printing, downloaded from web page: https://3dprintingindustry.com/about-us/ , Download date: May 2017, original posting date unknown, 4 pages.

Zdavprint: New 3D Printed Casts for Bone Healing, 3D Printing Pin, Feb. 2015, downloaded from web page: http://www.3dprintingpin.com/zdavprint-new-3d-printed-casts/, original posting date 2013, 5 pages.

Cortex, Evill, 2013, downloaded from web page : http://www.evilldesign.com/cortex, Download date: May 2017, Original posting date 2013, 12 pages.

Milionis, A., Noyes, C. Loth, E., and Bayer, I.S., Superhydrophobic 3D Printed Surfaces by Dip-Coating, 2014, NSTI-Nanotech 2014, vol. 2. pp. 157-160 (2014).

3DXTech Advanced Materials, Carbon Fiber ABS and PLA Test Data, Apr. 8, 2015, 3DXTech Advanced Materials Blog, pp. 1-3, (2015).

Paterson, A.M., Donnison, E., Bibb, R.J., and Campbell, I.R., Computer-aided design to support fabrication of wrist splints using 3D printing: A feasiblity study, 2014, Hand Therapy, vol. 19(4), pp. 102-113, (2014).

Quigly, E., A Few ways to strengthen 3D printed parts, Oct. 10, 2014, 3ders.org, pp. 1-19 (2014).

Karasahin, Deniz Osteoid Medical cast, attachable bone stimulator, 2014, A Design Award & Competion, pp. 1-4 (2014).

* cited by examiner

3-DIMENSIONAL AUGMENTED REALITY SCANNER FOR CUSTOMIZED MEDICAL IMMOBILIZATION DEVICES

CROSS-REFERENCE TO RELATED APPLICATIONS

The present application claims the benefit of U.S. Provisional Patent Application No. 63/601,662, filed Nov. 21, 2023 and titled, "3-Dimensional Augmented Reality Scanner for Customized Medical Immobilization Devices," the entire contents of which is incorporated herein by reference in its entirety.

BACKGROUND OF THE INVENTION

For decades, the medical field has sought to improve the methods used to treat limb and skeletal injuries, particularly in the field of orthotics and orthopedics. Traditional methods, often reliant on manual measurements and generic molds, have frequently resulted in inaccurate and uncomfortable casts, braces and splints (i.e. orthoses). These suboptimal fits can lead to discomfort, prolonged healing times, hygiene issues, and in some cases, complications due to inadequate support. Capturing the unique contours and nuances of individual limbs has been a challenge when utilizing traditional techniques, methods, materials and systems, thereby making it difficult to ensure that each treatment is as tailored to the individual patent and as effective as possible.

With the advent of advanced technologies like TrueDepth, light detection and ranging ("LiDAR"), augmented reality ("AR") and artificial intelligence ("AI"), there emerged an opportunity to revolutionize this domain. These technologies, initially developed for other industries, found a novel and impactful application in the medical sector. It would be desirable to design, develop, implement and deploy a scanner using advanced imaging technologies to customize orthoses for patients, thereby improving patient comfort and outcomes and tailoring treatment to the individual anatomy and injury of the patient.

BRIEF SUMMARY OF THE INVENTION

By harnessing the capabilities of LiDAR, AR, AI and TrueDepth in unique ways for the orthopedic industry, there is potential to create a system that scans limbs with unprecedented accuracy in three-dimensional space, paving the way for personalized treatments that prioritize patient comfort and optimal healing conditions. These updated treatments and techniques may also allow for real time prediction and simulation of immobilized limb alignment. This convergence of technology and medical expertise promises a new era of limb injury treatment, setting the stage for the development of 3D scanner systems that may be utilized in additive manufacturing to produce customized immobilization devices for each patient configured for the patient's anatomy and specific injury.

The three-dimensional ("3D") scanner system represents a groundbreaking convergence of advanced technologies tailored for the medical field. By seamlessly integrating the precision of TrueDepth and LiDAR technologies, the system captures the intricate details of limbs, ensuring a comprehensive scan and 3D model of the patient's limb. AR or Virtual Reality ("VR") enhances the user experience, overlaying virtual guides and cues during the scanning process.

Simultaneously, embedded AI algorithms analyze the data in real-time, optimizing the scanning process and ensuring unparalleled accuracy.

Post-scanning, the system processes the data, merging the detailed contours of the patient's individual anatomy from TrueDepth or with the broader depth map from LiDAR to create a holistic 3D model. This 3D model of the patient's limb serves as the foundation for designing immobilization devices having a custom fit for the patient. The immobilization devices may include splints, casts, braces and related orthoses tailored to the patient's unique anatomy. Advanced algorithms consider factors like injury type, limb orientation and patient customization such as color, imprinted and customized text on the cast or splint an additional customization, ensuring the resultant design is both functional and comfortable. The system's integration capabilities ensure it works in harmony with existing medical infrastructures, promising a future of personalized, efficient and effective limb injury treatment.

Briefly stated, a preferred embodiment of the present invention is directed to a system for 3D scanning and visualization for modelling an orthosis to a patient's limb. The system includes a scanning device including a LiDAR camera and a TrueDepth camera, reality glasses configured to modify the appearance of the limb, a charging console comprised of a station designed to provide power and replenish a battery, a central processor and a handheld station supporting the scanning device. The scanning device configured to capture detailed depth information from the limb. The central processor including a software interface configured as a digital platform tailored to process, analyze, and display data acquired by the scanning device. The central processor being in communication with the reality glasses. The handheld station configured to facilitate manipulation of the scanning device to acquire the data related to the limb.

In another aspect, a preferred embodiment of the present invention is directed to a system for scanning an object. The system includes a mechanism for secure mounting of a mobile device equipped with a LiDAR sensor or a TrueDepth camera, a scanning device equipped with a scanner LiDAR sensor or a scanner TrueDepth camera and a central processor. The mechanism configurable to allow the mobile device to traverse around the object, wherein the mobile device is configured to capture multiple angles and perspectives of the object or manually position or rotate the mobile device for scanning. The scanner LiDAR sensor and the scanner TrueDepth camera collectively scan the object with the mobile device. The central processor includes integrated software to process, merge, and analyze data from the mobile device and the scanning device and generate a 3D representation of the object. The scanning device may be in communication with a scanning software and an augmented reality platform configured to validate fitting of the orthosis.

The virtual reality glasses of the preferred embodiment may be comprised of wearable eyewear that immerses a user in a virtual environment. The augmented reality glasses may be comprised of wearable eyewear that overlays digital information onto real world objects. The scanning device may include a laser-assisted device.

The software interface may be configured to display an instructional presentation, educating users about fitting, benefits and usage of the orthosis. The software interface may be configured to allow users to digitally customize an appearance of the orthosis, wherein the orthosis is customized with respect to color, lattice and/or engravings. The charging console may be configured to provide power to both the scanning device and the reality glasses. The software interface may be configured to provide real-time corrections to a position of the limb during a scanning process. The software interface may be configured to display an avatar that guides a user through the scanning process. The software interface may be configured to provide fitting and sizing options for the orthosis. The software interface may be configured to facilitate visualization of the orthosis on the limb with options to select different colors and designs for the orthosis. The software interface may be configured to facilitate customization of the orthosis, including cutouts, straps and/or eyelets.

The scanning device may be configured to simultaneously scan with two or more users. The scanning device may be configured for adjustment in height, curvature, and/or length based on a desired point of view and degree of freedom in the scanning process. The laser-assisted device may be configured to be set as a boundary of the scanning device to assist the scanning process.

The preferred system may include an enclosure for the scanning device. The preferred enclosure includes an adjustable handle. The adjustable handle may be configured to facilitate positioning of the scanning device for scanning the limb. The adjustable handle may include multiple buttons configured to provide access to various scanning functions during a scanning process. The multiple buttons preferably include a shutter activation button, a laser toggling button, and a boundary setting button.

The system may be configured to scan a contralateral limb of the limb and simulate an alignment of the limb. The alignment may be overlaid on the limb using augmented reality of the central processor and visually demonstrating differences and potential post-treatment outcomes.

BRIEF DESCRIPTION OF THE SEVERAL VIEWS OF THE DRAWINGS

The foregoing summary, as well as the following detailed description of preferred embodiments of the instrument, implant and method of the present application, will be better understood when read in conjunction with the appended drawings. For the purposes of illustrating the 3D augmented reality scanner system and resulting customized immobilization devices, there are shown in the drawings preferred embodiments. It should be understood, however, that the preferred invention is not limited to the precise arrangements and instrumentalities shown. In the drawings.

DETAILED DESCRIPTION OF THE INVENTION

Figures 1A, 1B:
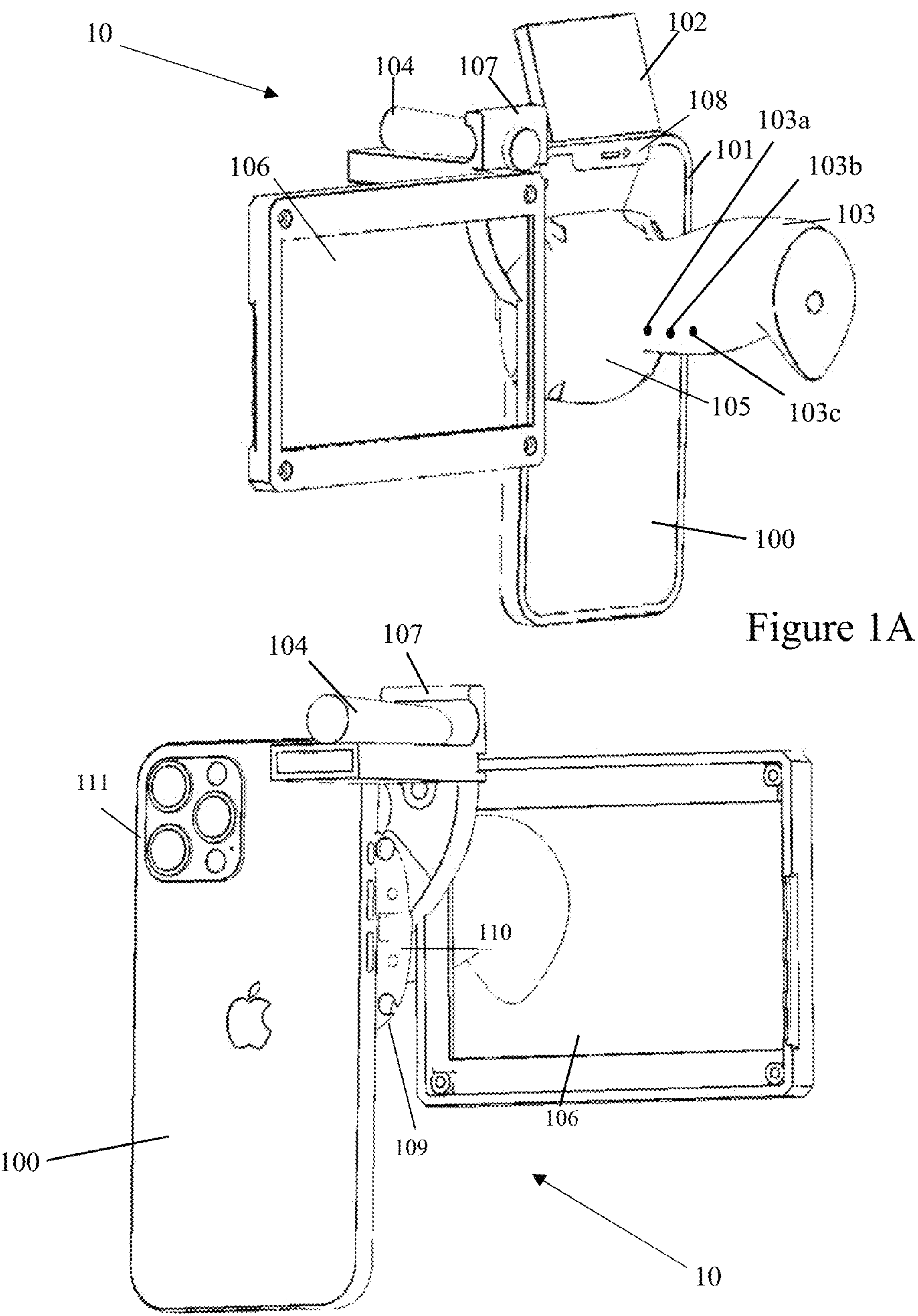
FIG. 1A illustrates a rear perspective view of a 3D scanner system that contains a Lidar/true depth camera, mirror, portable screen, handle, pointer and angle pitch in accordance with a preferred embodiment of the present invention.
FIG. 1B illustrates a front perspective view of the 3D scanner system of FIG. 1A.

Certain terminology is used in the following description for convenience only and is not limiting. Unless specifically set forth herein, the terms "a", "an" and "the" are not limited to one element but instead should be read as meaning "at least one". The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred 3D augmented reality scanner system and resulting customized immobilization devices and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1A-4, a preferred 3D scanner system, generally designated 10, represents a technological advancement in the medical field. Designed with precision and user experience in mind, the 3D scanner system 10 seamlessly merges the capabilities of TrueDepth or LiDAR technologies, ensuring a comprehensive scan of limbs to create a 3D model of the patient's limb 303 and subsequently design and mount a cast, brace or other orthosis 404 to the patient's limb 303 to promote healing. This convergence of technologies, further enhanced by AR visualization, ensures that the scanning process is not only accurate but also interactive and user-friendly, setting a new standard in medical scanning solutions.

Traditional methods of limb scanning and casting often rely on generalized measurements, which can lead to discomfort and prolonged healing times when the final cast or brace 404 does not fit the user's limb 303 property, as patient's often have unique anatomic features and irregularities. Every individual's limb 303 is unique, with distinct contours, lengths, and circumferences and injuries can further exacerbate anatomical distinctions. The preferred 3D scanner system 10 recognizes this diversity and is designed to capture nuances of the patient's limb 303. This attention to detail ensures that the resultant braces, casts or splints 404 are tailored to the individual patient and the specific anatomy of the patient's target limb 303, thereby promoting comfort and optimal healing conditions.

TrueDepth technology, which is preferably incorporated into the 3D scanner system 10 by a TrueDepth camera 108, 201, was initially designed for facial recognition in consumer electronics, but the preferred 3D scanner system 10 utilizes the TrueDepth camera 108, 201 in the medical field to dimension the patient's limb 303. By projecting a dense array of infrared ("IR") dots onto a surface, the TrueDepth technology, camera or scanner 108, 201 captures minute details or a surface of the limb 303 that might be overlooked by other scanning methods. The TrueDepth camera 108, 201 may be incorporated into a scanning device 100, which may be comprised of a smartphone or other mobile device 100. The scanning device 100 may be customized for use with the 3D scanner system 10 or may be comprised of the smartphone 100 that is designed and configured for use with the 3D scanner system 10. The strength of the TrueDepth technology, which is preferably employed through the TrueDepth camera 108, 201, lies in its ability to measure the distortion of the IR dots that are projected onto the patient's limb 303. As the IR dots project onto the surface or skin of the patient's limb 303, their distortion is captured by a specialized camera or the TrueDepth camera 108, 201. The capture of this data by the TrueDepth camera 108, 201 provides a wealth of information regarding the shape and configuration of the limb 303, allowing for the creation of a detailed 3D model or representation of the limb 303. Depth sensing is also preferably utilized with the TrueDepth camera 108, 201. The infrared TrueDepth camera 108, 201 of the TrueDepth technology in the 3D scanner system 10, preferably captures the pattern of the projected dots, and based on their distortion, calculates the depth at multiple points on the surface of the limb 303. This granular data, when processed, forms a detailed 3D map of the limb 303. This map captures intricate features of the limb 303, ensuring that the resultant cast, brace or splint 404 is custom fit to the individual patient's limb 303 based on modelling the cast, splint, brace or other orthoses 494 over or onto the 3D map of the limb 303.

The 3D scanner system 10 includes a light detection and ranging ("LiDAR") camera 111 that preferably utilizes LiDAR technology. The LiDAR technology is a technology that has been employed in various industries, from archaeology to autonomous vehicles. In the context of the 3D scanner system 10, the LiDAR camera 111, which is preferably incorporated into the scanning device 100, offers rapid and broad scanning capabilities. The scanning device 100 may be comprised the user or patient's smartphone 100 but is not so limited. By emitting laser beams and measuring the time taken for them to reflect back to their source, the LiDAR camera 111 calculates depth over vast areas, particularly depth of the surface or skin of the patient's limb 303 from the source of the LiDAR camera 111 and transmits this collected data to the central processor 203. This rapid scanning ensures that while the finer details of the surface features of the patient's limb 303 are captured by the TrueDepth camera 108, 201, the overall shape and size of the limb 303 are captured by the LiDAR camera 111.

The strength of the LiDAR camera 111 with the 3D scanner system 10 lies in its ability to provide a macro view of the limb 303. The emitted laser beams, when reflected back, provide time-of-flight data. This data, when processed by the central processor 203, gives a broad depth map of the limb 303. This depth map, while not as detailed as the one from the TrueDepth camera 108, 201, provides a context for the limb 303. When combined with the data from the TrueDepth camera 108, 201, the combined data ensures a holistic and comprehensive 3D model of the limb 303.

The integration of the TrueDepth and LiDAR cameras 108, 111, 201, 202 in the 3D scanner system 10 is preferred for defining the 3D model of the patient's limb 303 so that the orthosis 404, which may be comprised of a custom cast, brace, support or other orthosis 404, may be custom constructed to fit the patient's unique limb 303. While the TrueDepth camera 108, 201 provides a micro-level view of the limb 303, capturing the intricate details of the limb 303, the LiDAR camera 111 offers a macro-level view, ensuring that the overall shape and context of the limb 303 are not missed. The resultant data from both the TrueDepth and LiDAR cameras 108, 111, 201, 202 is meticulously fused in the system's processing unit, central processor or 3D Processing 203. This fusion ensures that the 3D model created by the central processor 203 is both detailed and comprehensive, serving as a blueprint for the design of the orthosis 404, which may be comprised of a splint, brace or cast 404, for a custom fit virtually over the 3D model of the patient's limb 303.

Figure 2:
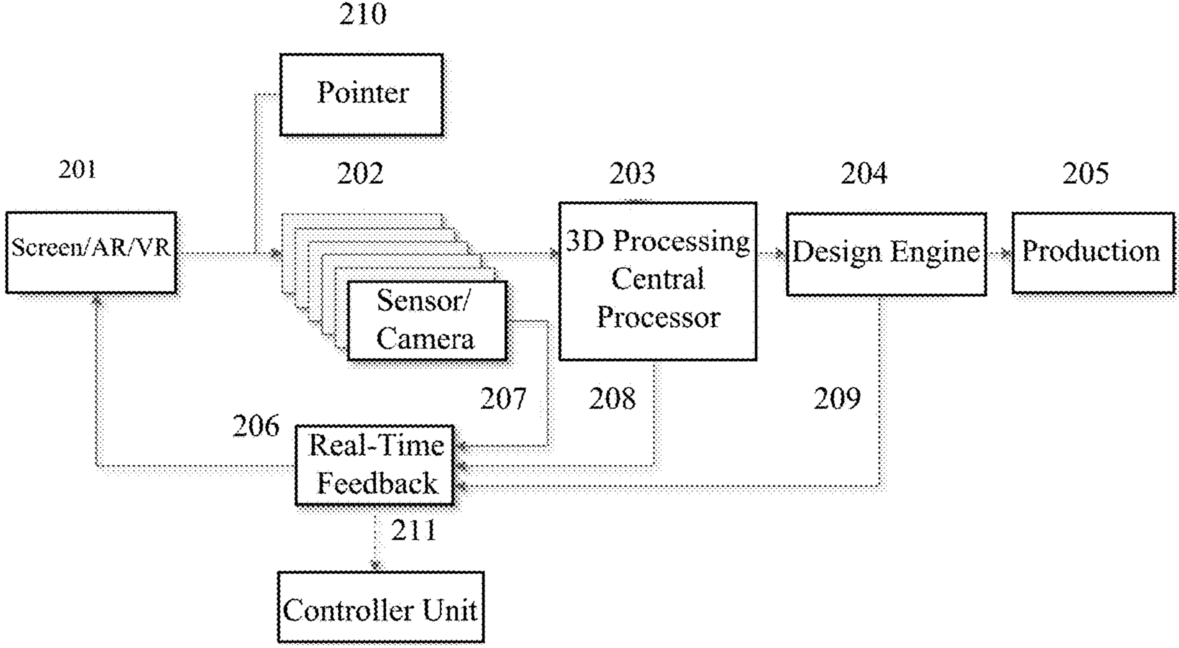
FIG. 2 illustrates a workflow from scan to production containing real feedback toolkits, AR/VR, pointer and sensor inputs, and a controller unit in accordance with a preferred embodiment of the present invention.
Figure 3:
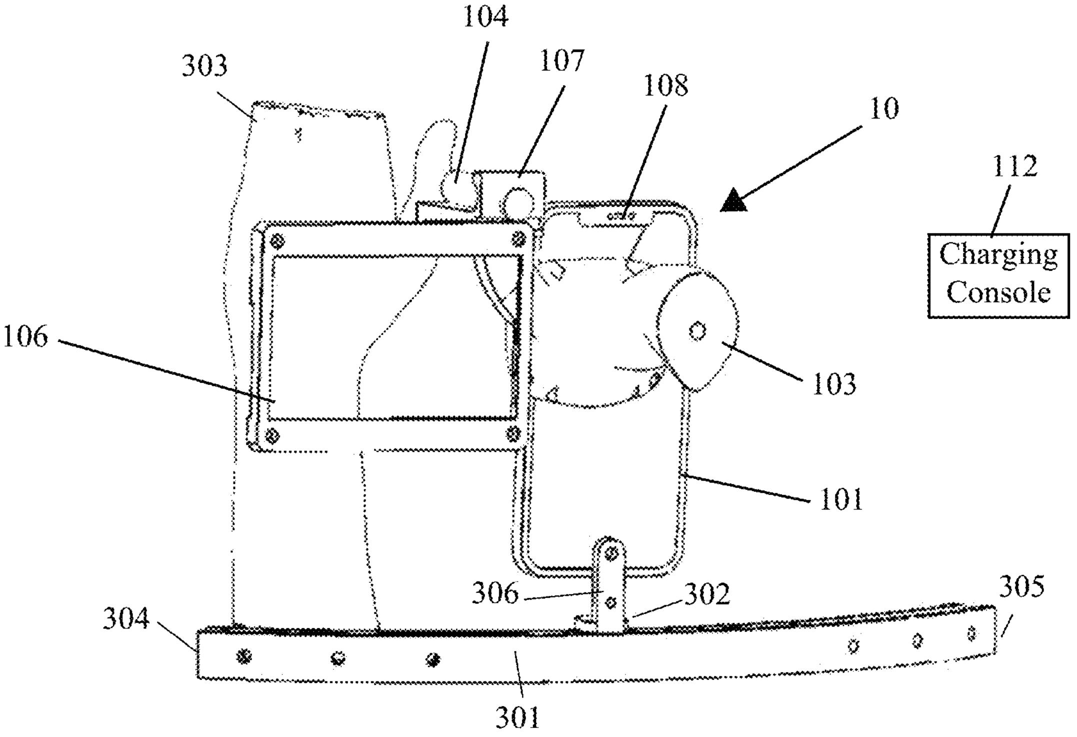
FIG. 3 illustrates a rear perspective view of an adjustable motion mechanism with a station for use with the 3D scanner system of FIG. 1A in a scanning mode, wherein the 3D scanner system is mounted to a rail in accordance with a preferred embodiment of the present invention.

Referring specifically to FIGS. 1A-2, the preferred 3D scanner system 10 may include a pointer 104, 210, a mirror 102, an extra screen 106 for screen mirroring, a handle 103 with a base 105 proximate the scanning device or smartphone 100, a device engagement mechanism 101, and a charger or battery 107. The pointer 104, 210 is preferably utilized for guiding, accuracy, and distance validation. The mirror 102 can be installed to have full vision of a front camera while the user is experiencing the TrueDepth camera 108, 201. Moreover, the extra screen 106 can assist with the screen mirroring. The 3D scanner system 10 may utilize the engagement mechanism 101, which is preferably attached to the handle 103, to engage and align the scanning device 100, such as the user's smartphone 100, for imaging purposes. The handle 103 is shown extending generally perpendicular relative to a large flat surface of the smartphone 100 but is not so limited and may have alternative designs and configurations, as long as the user is able to manipulate the 3D scanner system 10 relative to the limb 303 for imaging purposes. The handle 103 may also be stationed at multiple angles relative to the scanning device or smartphone 100 and extra screen 106 for capturing various points of view during the 3D scanning process. The 3D scanner system 10 may include a pivot hinge 110 to manipulate the orientation of the handle 103 relative to the scanning device or smartphone 100 with locking holes 109 to facilitate locking of the orientation of the scanning device or smartphone 100 and handle 103 relative to the extra screen 106. The pointer 104 is preferably set to the charger or battery 107.

Figure 4:
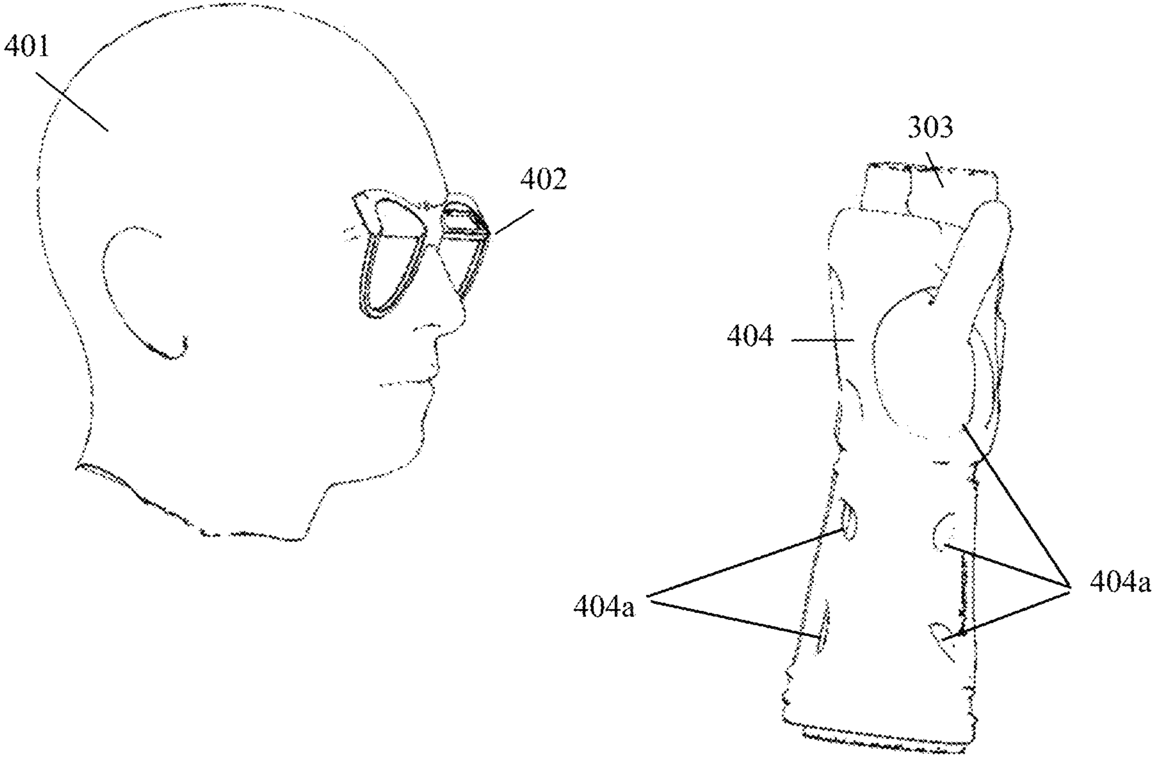
FIG. 4 illustrates side perspective views of AR/VR glasses, an appended orthotic device engaged with a user's arm and hand in a mounted configuration, a user, and the patient's limb in accordance with the preferred embodiment of the present invention.

Referring to FIG. 4, in the preferred embodiment, AR may add an interactive layer to the scanning process utilizing the 3D scanner system 10. Through specialized AR glasses or displays 402, the 3D scanner system 10 overlays virtual guides, grids, and visual cues directly onto the patient's limb 303 to prompt the user regarding scanning of the limb 303. This real-time feedback ensures that the patient and the medical professional are in sync during the scanning process and the patient or medical professional collects adequate data during the scanning process to construct the 3D model of the limb 303. These AR overlays of the AR glasses or displays 402, which may alternatively be depicted on the extra screen 106, may assist the patient 403 or a medical professional/technician 401 in guiding the scanning process with the 3D scanner system 10. Whether it's adjusting the orientation or angle of the limb 303 relative to the 3D scanner system 10, the position of the extremity or limb 303 to a position desired for a proper cast or other orthosis 404, repositioning the cast, brace or orthosis 404 or the limb 303, or ensuring that the limb 303 remains steady during scanning, the AR guides and/or prompts the user during operation. The AR glasses or displays 402 may provide visual cues, making the scanning process and the application of the orthosis 404 to the patient's limb 303 intuitive, user-friendly and accurate.

Referring to FIGS. 1A-4, proper positioning of the limb 303 is preferred for an accurate scan of the patient's limb 303 using the 3D scanner system 10. The AR glasses or display 402 component of the 3D scanner system 10 may improve this by providing real-time visual feedback 206. If the limb 303 needs to be tilted or rotated, the AR glasses or display 402 may overlay and provide clear visual instructions to the user or the patient, ensuring that the scan captures all the necessary data. Beyond just positioning, the AR glasses or display 402 may also provide visual feedback on the scanning progress. For instance, areas that have been successfully scanned are highlighted in green on the glasses or display 402, while areas that need rescanning could flash red. This real-time feedback preferably ensures that the scanning process is both thorough and accurate 207.

AI is preferably utilized with the 3D scanner system 10, preferably during data analysis and collection in a control unit or central processor 203. The AI is preferably embedded within the 3D scanner system 10 such that the AI continuously analyzes the incoming data, ensuring that the scanning process is optimized at every step and provides feedback 206. Trained on vast datasets of limb scans, the AI is preferably able to predict potential issues with the scanning and/or modelling even before issues arise. Whether it's suggesting a repositioning of the limb 303, optimizing the scanning angle 207 or modelling feedback 209, the AI preferably ensures that the scanning process is providing an accurate scan and model of the limb 303. Moreover, the AI preferably assists the patient to hold the limb 303 in specific positions for the required prescribed orthosis to ensure accurate data capture and modelling for construction of the orthosis 404.

A feedback step 209 provides an innovative approach for clinicians to enhance patient care by integrating patient data directly into the treatment process. This feature allows medical professionals to append patient information, including medical imaging such as MRI and CT scans, directly into the central processor 211 for incorporation into the 3D model and ultimately into the orthosis 404, such as a hand immobilization device. This integration improves the sizing and fit of the orthosis, splint or cast 404 and may facilitate the tailoring of the orthosis, splint or cast 404 to address specific medical needs by the 3D scanner system 10. By having immediate access to relevant patient data and imaging, clinicians can make informed decisions about the suitability of the immobilization device or orthosis 404, particularly in terms of stabilizing fractures, managing swelling, and treating wounds.

Furthermore, this unique capability of the 3D scanner system 10 to incorporate patient-specific data and imaging directly onto the orthosis, splint or cast 404 represents an advancement in personalized medical care. It facilitates a more efficient and effective treatment process, allowing for real-time adjustments and optimizations based on the patient's current medical condition. This feature of the 3D scanner system 10 is particularly beneficial in complex cases where the management of fractures, swelling, and wound care requires careful consideration and continuous monitoring, for example for burns where the skin is treated during the healing process. The integration of patient data and medical images onto the immobilization device, orthosis, splint or cast 404, thus ensures a higher standard of care, tailored to the individual needs of each patient. For example, cavities or holes **404*a* may be positioned in the orthosis 404 at areas where the patient's skin is burned to expose the burned skin for treatment while the orthosis 404** is in the working configuration.

As the scanning progresses, the AI in the central processor 211 is preferably monitoring the data and providing real-time feedback 206. The AI preferably, continuously analyzes the data, looking for anomalies or potential errors. If a particular area of the limb 303 hasn't been captured properly, the AI preferably provides feedback to the controller unit or central processor 211, which preferably ensures that the medical professional or the controller unit 211 itself can address the issue in real-time 209 by providing a message to the patient to collect additional data. This real-time analysis by the AI is preferred to ensure efficiency of the scanning process 208. By addressing issues or errors as they arise, the 3D scanning system 10 preferably ensures that the resultant 3D model is both accurate and comprehensive. Post-processing is another alternative to deform, smooth, or run any other preferred functions that will be performed with a design engine 204.

Once the scanning of the limb 303 is finished, the 3D scanning system 10 enters a data fusion phase. In the date fusion phase, the detailed data from the TrueDepth camera 108, 201 and/or the LiDAR camera 111 are preferably, seamlessly merged by the controller unit or central processor 211. Advanced algorithms ensure that this fusion preferably results in a comprehensive 3D model of the limb 303 or other impacted area of the patient's body. The 3D model serves as a foundation for the subsequent design and production phases. By ensuring that the preferred model is both detailed and holistic, the 3D scanning system 10 improves the custom shape and size of the resultant splint, orthosis or cast 404, so that the orthosis 404 is custom tailored to the patient's unique anatomy and conforms to the size and shape of the patient's limb 303.

With the 3D model, the 3D scanning system's 10 design patterns the orthosis 404 based on the required template and individual scans 203, 204. The algorithms of the control unit or central processor 211 preferably take into account factors like the nature of the injury, the specific part of the limb 303, the patient's comfort and specific customization to design the orthosis, splint or cast 404 to have improved functionality and comfort for the patient. The design process is preferably iterative. The 3D scanning system 10 may create multiple design prototypes, analyzing each for optimal pressure distribution, ventilation, and support on the patient limb 303, such as the patient's hand, arm or wrist, with AR. The preferred design is then finalized by the control unit 211, thereby preferably ensuring that the patient receives the best possible care. The control unit 211 may also consider patient data input by a medical professional or from the patient's medical records, in addition to the scan data and the 3D model, to develop the 3D model and the final custom orthosis 404. Such additional patient data may include skin conditions, type of injury, age, sex, weight, height and other personal or medical data related to the patient 403.

Every patient 403 is unique, and so is each patient injury. The 3D scanning system 10 preferably recognizes this diversity and ensures that every design aspect is tailored to the individual patient's needs and the needs of the patient's unique limb 303 and injury. Whether it's the placement of ventilation holes **404*a* in the orthosis 404, the distribution of pressure points on the orthosis 404, inclusion of mobility sections in the orthosis 404, color, printed logos or names or even the overall shape of the orthosis, splint or cast 404, the 3D scanning system 10 preferably ensures personalization at every step. Beyond just the design, the 3D scanning system 10 also preferably takes into account the patient's lifestyle and activity levels. For instance, an athlete might require a more rigid cast, while a sedentary individual might benefit from a more low-impact immobilization device such as a more flexible or light-weight splint or orthosis 404. The 3D scanning system 10 preferably ensures that these considerations are factored in, preferably resulting in optimal healing conditions. In addition, as another example, a patient who swims may desire a waterproof orthosis 404 or an orthosis 404 that may be removable during activity and the 3D scanning system 10 may accommodate this and similar specific desires and requirements of the particular patient 403**.

The choice of material for the orthosis 404 is also preferably selected or suggested by the 3D scanning system 10, particularly the central processor 211. Different injuries may require different materials for the orthosis 404, and the 3D scanning system 10, with its preferred vast database in the control unit or central processor 211, is preferably equipped to recommend a material for every scenario. Factors like rigidity, breathability, and comfort are preferably considered by the 3D scanning system 10. The thickness of the cast or orthosis 404 may be varied by proportions of the attention anatomy 209 and thickness or materials for the orthosis 404 may be modified to customize strength, stiffness, durability or other factors of the orthosis 404.

Additionally, AR technology, which is preferably comprised of a module in the central processor 211, preferably offers the capability to assess a person's range of motion while also allowing for the establishment of exclusion angles for articulating braces or other orthoses 404. The 3D scanning system 10 is preferably able to precisely determine the limits and constraints of the anatomical motion of the limb 303, thereby limiting the range of motion of the patient's limb 303 at a joint, such as to not exceed certain angles or positions that might be detrimental to the user's safety or recovery. This innovative application of the AR technology not only enhances the effectiveness of articulating braces or other orthoses 404 but also contributes to the overall advancement of healthcare technology, providing more tailored and responsive solutions for patients with mobility issues.

With the design and material finalized, the 3D scanning system 10 preferably moves to the production phase. Here, advanced machinery, which may include a 3D printer or subtractive machining technology 205, crafts the final production orthosis, splint or cast 404. Precision is preferred in this phase to take advantage of the customized 3D model to fit the patient's specific limb 303. The machinery ensures that the contours, ridges, and features from the 3D model, which is translated into a model of the orthosis 404, is preferably replicated in the final orthosis 404, producing a desired fit for the patient 403. The 3D scanning system 10 is preferably designed for rapid iteration. If issues arise, the design of the final orthosis 404 can be quickly modified, and a new orthosis, splint or cast 404 can be produced, ensuring that the patient's comfort and healing are prioritized.

Quality assurance is also preferably incorporated into the 3D scanning system 10. Once the orthosis, splint or cast 404 is produced, the orthosis 404 preferably undergoes rigorous checks. Advanced imaging systems, integrated within the 3D scanning system 10, preferably compare the final orthosis 404 against the original final design developed by the 3D scanning system 10. These checks may include scanning the manufactured orthosis 404 with the 3D scanning system 10 to confirm the size and shape of the orthosis 404 complies with the designed orthosis 404. Any discrepancies between the final design and the final orthosis 404, however minor, are preferably flagged by the central processor 211. If required, the 3D scanning system 10 can iterate on the design and production, ensuring that the final product or orthosis 404 matches the desired requirements of the designer or medical professional.

In today's interconnected medical landscape, standalone systems are a rarity. Recognizing this, the 3D scanner system 10 is preferably designed for seamless integration with other systems typically employed in the healthcare environment. Whether it's interfacing with an orthotic room, occupational therapy, hospital's electronic health record system, integrating with imaging tools, connecting with telehealth platforms or other healthcare systems, the 3D scanning system 10 preferably ensures cohesive operation by communicating with these systems through the central processor 211. This integration preferably results in the patient's medical history, previous scans, and other relevant data being accessible to other healthcare providers and systems to provide enhanced care for the patient. By ensuring that all relevant data is at the fingertips of the medical professionals, the 3D scanning system 10 promotes informed decision-making by healthcare professionals at every step of the patient's care.

The mobile 3D scanner system 10 is preferably adaptable into or may be utilized with the rail 301, remote controller 302 and adjustable heightening system 306, which promote consistent scanning of the limb 303. The stationary 3D scanner system 10 is preferably mounted to the rail 301, which guides the 3D scanner system 10 to scan the limb 303 with a preferred degree of freedom in a preferred point of view. The rail 301 may be adjusted between first and second ends 304, 305 and settled on any flat, stand or other support. A rail length, measured between the first and second ends 304, 305, and curvature of the rail 301 is preferably flexible and adjustable depending on the required visibility and interested or injured region of the limb 303. The 3D scanner system 10 is preferably attached to the rail 301 via the adjustable heightening system 306 and the remote controller 302. The remote controller 302 preferably automatically captures the required data. The controller 302 may include a motor that drives the 3D scanner system over and along the rail 301 at a predetermined speed while the scanning of the patient's limb 303 is processing.

The 3D scanner system 10, with its amalgamation of technologies and user-centric design, is preferred for use in the treatment of limb injuries. By enhancing precision, personalization, and integration, the 3D scanner system 10 promotes a future where every patient receives care that is tailored to their unique needs, such as treatment to the lower extremities, arm, hand, wrist or torso. As technology continues to evolve, the 3D scanning systems 10 has the potential of merging medical expertise with technological prowess. The future of medical care is not just about treating ailments but doing so in a manner that prioritizes the individual, and the preferred 3D scanning system provides a patient centric device, system and method for personalized orthopaedic care.

The 3D scanner system 10 is configured for 3D scanning and visualization for modelling the orthosis 404 to the patient's limb 303. The orthosis 404 may be comprised of a cast, splint, brace or other orthosis secured to the patient's limb 303 to promote healing. The scanning device 100 includes the LiDAR camera and the TrueDepth camera 111 and is configured to capture detailed depth information or data from the patient's limb 303. The scanning device 100 is in communication with the central processor 203 for transmission of the acquired data and, preferably, for transmission of messages and information from the central processor 203 to the scanning device 100.

The preferred scanning device 100 includes a laser-assisted device. The scanning device 100 may be configured to scan with two or more users, such as a clinician, child, parent, patient or other such users. The scanning device 100 may include an enclosure, which may include the engagement mechanism 101 and the handle 103, wherein the handle 103 is connected to the engagement mechanism 101 at the handle base 105. The handle 103 may be adjustable with multiple ergonomically positioned buttons 103*a*, 103*b*, 103*c* configured to provide access to various scanning functions of the scanning device 100 during a scanning process. The multiple buttons 103*a*, 103*b*, 103*c* may include a shutter activation button 103*a*, a laser toggling button 103*b* and a boundary setting button 103*c*, although these buttons 103*a*, 103*b*, 103*c* are not limiting and the system 10 may include alternate and additional buttons for manipulating and controlling the scanning device 100.

The system 10 for 3D scanning also includes the reality glasses 402 that are configured to modify the appearance of the limb 303 when observed by the wearer of the reality glasses 402, which may be the medical professional/technician, the user or the patient 401. The reality glasses 402 may be comprised of augmented reality glasses or virtual reality glasses 402. The virtual reality glasses 402 may be comprised of wearable eyewear 402 that immerses a user in a virtual environment and displays the 3D model of the patient's limb 303, the orthosis 404 and/or other features of the limb 303 and orthosis 404. The augmented reality glasses 402 may be comprised of wearable eyewear 402 that overlays digital information, such as the 3D model of the orthosis 404, onto real world objects, such as the limb 303. The system 10 is not limited to including the reality glasses 402 but the reality glasses 402 are preferred to provide visualization of the limb 303 and/or the orthosis 404 for the clinician, medical professional, user, patient or other individual who wears the reality glasses 402. The reality glasses 402 are preferably in communication with the central processor 203 to transmit data related to the 3D model of the orthosis 404 and/or limb 303 for presenting the augmented or virtual reality environments onto the lenses of the reality glasses 402. In a non-limiting example, the reality glasses 402 may be configured to display or present a real-time visualization of the limb 303, which may be comprised of the user's hand, wrist and forearm, overlaid with a virtual representation of the orthosis 404.

The 3D scanner system 10 also includes a charging console 112 comprised of a station designed to provide power and replenish batteries, such as the battery 107. The charging console 112 is also preferably configured to provide power to the scanning device 100 and the reality glasses 402. The charging console 112 may be designed and configured to charge, power or recharge nearly any of the equipment of the 3D scanner system 10.

The 3D scanner system 10 includes the central processor 203 including a software interface or module configured as a digital platform and tailored to process, analyze and display data acquired by the scanning device 100. The central processor 203 is in communication with the reality glasses 402. The central processor 203 may be in communication with the scanning device 100 via wireless or wired communication protocols to transmit data to and from the central processor 203 and the scanning device 100.

The software interface of the central processor 203 may be configured to allow users to select from different types of appendages, such as straps, harnesses and related features, and structural designs for the orthosis 404, which may be comprised of a cast, brace, splint or other support. The software interface may be configured to provide telehealth features, enabling the medical professional to remotely validate fitting of the orthosis 404. The software interface may be configured to display an instructional presentation to educate users, patients or other medical professionals about fitting, benefits and usage of the orthosis 404. The instructional presentation may be comprised of a video, training module, simulation or other information about the 3D scanning system, orthosis 404 or other feature of the 3D scanning system 10. The software interface may further utilize a mix of data acquired from the TrueDepth and LiDAR cameras 108, 201, 111 for enhanced scanning accuracy and depth perception of the 3D model of the limb 303 and/or orthosis 404. The software interface of the central processor 203 may also be configured to allow users to digitally sign or customize an appearance of the orthosis 404, wherein the orthosis 404 may be customized with respect to color, lattice, engravings, holes 404*a* or other features that facilitate customization of the orthosis 404 by the user or medical professional. As a non-limiting example, the orthosis 404 may be customized to include a company logo, patient signature, patient preferred color scheme or other custom features that may be desired by the patient and/or medical professional.

The software interface may further be configured to provide interactive features for pediatric users, including how to use the 3D scanner system 10, animations, interactive avatars guiding the pediatric users through a scanning process, interactive AI-assisted process/avatar to assure the limb 303 is in a correct or preferred positioning during the scanning process or other features to assist the patient. The software interface may further be configured to display a position outline of the limb 303 or a 3D model of the limb 303 during a scanning process to inform the user or clinician regarding portions of the limb 303 that may require additional scanning and which portions are included in the 3D model of the limb 303. The software interface may further be configured to allow users to adjust a positioning of the limb 303 post-scan using artificial intelligence associated with the central processor 203. The software interface may further be configured to provide real-time corrections to a position of the limb 303 during a scanning process such that the scanning device 100 is able to acquire sufficient data to develop the 3D model of the limb 303 for subsequent design of the orthosis 404. The software interface may further be configured to display an avatar of the patient or the patient's limb 303 that guides a user through a scanning process, such as by providing instruction to the patient or medical professional regarding how to scan the limb 303 with the scanning device 100.

The software interface may further be configured to enable a remote provider or technician to join a scanning session with the patient and/or medical professional and assist with positioning of the limb 303. The remote provider or technician may join the scanning session through the scanning device 100, which may be comprised of the user or patient's smartphone 100, to direct and inform the patient and/or medical professional regarding the scanning process. The software interface may further be configured to simulate the orthosis 404 positioned on the limb 303 in various scenarios, including sports practice and vocational requirements. The simulation of the orthosis 404 and the limb 303 is preferably based on 3D models of the orthosis 404 and limb 303 generated by the central processor 203 based on the data acquired by the scanning device 100 during the scanning process. The software interface may further be configured to provide fitting and sizing options for the orthosis 404 based on the 3D model developed by the central processor 203. The 3D model of the orthosis 404 may represent a brace, cast, splint or various other orthopedic devices fit to the patient's limb 303.

The software interface may be configured to display medical images including at least one of X-rays, computerized tomography (CT), and magnetic resonance imaging (MRI) of the limb 303 for review by the patient and/or medical professional. The limb 303 may be comprised of various body parts, such as a hand, wrist, forearm, elbow, shoulder, foot, ankle leg, hip, back, neck or other body parts. The medical images, which may be from the patient's medical records and transmitted to the central processor 203, is preferably utilized to assist visualization or recognition of a pathology, wound management, predicting possible inflammation, confirmation of coverage of an injury or other features. The medical images may also be utilized as feedback for a clinician when customizing the orthosis 404 for the limb 303. The software interface may also be configured to facilitate visualization of the orthosis 404 on the limb 303 with options to select different colors and designs for the orthosis 404.

The software interface may be configured to facilitate customization of the orthosis 404, including at least one of cutouts or holes 404*a*, straps, and eyelets incorporated into the orthosis 404 for breathability, access to the patient's skin, fastening or parts of the orthosis 404 together or other features. The scanning device 100 may include a laser-assisted device that is attached to a sensor to guide a scanning process, validate a required resolution, and provide convergence of focus when single or multiple lasers are used with the scanning device 100. The lasers-assisted device may be configured to be set as a boundary of the scanning device 100 to assist the scanning process of the limb 303.

The central processor 203 includes an augmented reality (AR) environment or module in conjunction with artificial intelligence (AI) that may be configured to provide real-time visual feedback to the user, patient or medical provider. The visual feedback may be configured to predict limb deformation and suggest optimal positioning of the limb 303 during a skeletal reduction procedure to the medical provider, which may be displayed on the smartphone 100 or an alternative display based on messages from the central processor 203. The skeletal reduction procedure may include setting a fracture of the limb 303 or adjusting a bone of the limb 303. The visual feedback may include visual aids within the augmented reality environment, including initial and predicted X-ray images of the limb 303.

The central processor 203 may include an alternate reality environment including one of an augmented reality ("AR") environment and a virtual reality ("VR") environment. The reality environment may be configured to visually represent a stepwise design, wherein the stepwise design configured to aid in determining a number of adjustments needed and facilitate modification of a design of the orthosis 303. As a non-limiting example, the reality environment may represent the stepwise design for procedures or sequential treatment with different orthoses 303 to slowly correct a deformity of the limb 303. The stepwise deformity correction may include serial casting of the limb 303 to correct or limit the deformity.

The 3D pointer 104, 210 is preferably in communication with the central processor 203. The 3D pointer 104, 210 may be configured to interact within the AR and VR environments, such as to identify areas of interest of the limb 303, including pain points, injuries, wounds, burns, deformities and other markers on the limb 303.

The 3D scanner system 10 may be configured to scan a contralateral limb or non-injured side (not shown) of the limb 303 and simulate an alignment of the limb 303. The central processor 203 may communicate with the patient or medical professional to scan the contralateral limb with the scanning device 100 and this scanned data may be utilized to construct a 3D model of the contralateral limb. The contralateral 3D model may be mirrored or otherwise manipulated and overlaid onto the limb 303 using augmented reality of the central processor 203 to visually demonstrate differences and potential post-treatment outcomes for the limb 303. The contralateral limb 3D model may also be utilized to compensate for injury, deformity, swelling or other features of the limb 303 to develop a treatment plan for the limb 303.

The central processor 203 may be configured to determine a range of motion of the limb 303, particular for articulating joints associated with the limb 303 such as the wrist, elbow, shoulder, hip, knee, ankle, back or neck, based on the data acquired by the scanning device 100. The central processor 203 may be configured to set restrictions and exclusion angles for articulating devices of the orthosis 404, which are preferably designed into the custom orthosis 404. The limb 303 may be comprised of an arm with an elbow and the 3D scanner system 10 may be configured to restrict elbow flexion beyond a predetermined degree and limit the range of motion of the patient's arm with limitations designed into the orthosis 404. The range of motion may be limited for specific tasks performed by the patient, ensuring that the patient's mobility is safe and functional for the specific limb 303 to facilitate healing.

The 3D scanning device 10 and the central processor 203 may be in communication with a scanning software and an augmented reality platform configured to validate fitting of the orthosis 404. The orthosis 404 may be configured for visual inspection related to fit, pain points, and feedback, ensuring maximum comfort and functionality for the patient based on the augmented reality platform utilized by the 3D scanning device 10. The scanning software may support multi-user access, wherein the multi-user access is configured to allow multiple stakeholders to share an augmented reality space to evaluate the orthosis 404. The multiple stakeholders may include clinicians, patients, and designers and the augmented reality space may be configured to allow the clinician to view the orthosis 404. The augmented reality space is preferably configured to facilitate simultaneous style and design adjustments of the orthosis 404, thereby ensuring a collaborative approach to treatment.

The 3D scanner system 10 may include the mirror 102 that is configured for real-time feedback, screen mirroring, and user visualization settings.

The 3D scanner system 10 also includes a handheld station, which may include the engagement mechanism 101, the handle 103, the pivot hinge 110, the rail 301 and other components, supporting the scanning device 100 and facilitating the scanning process. The handheld station may be configured to facilitate manipulation of the scanning device 100 to acquire the data related to the limb 303.

The 3D scanning system 10 may also be utilized to scan an object, which is not limited to the limb 303. The 3D scanning system 10 includes a mechanism, such as the handle 103, engagement mechanism 101, the pivot hinge 110, the rail 301 and/or other components, for secure mounting of the scanning device 100. The scanning device 100 is equipped with a LiDAR sensor or a TrueDepth camera. The mechanism is used to securely install the scanning device 100, such as the smartphone 100. The mechanism is configurable to allow the scanning device 100 to traverse around the object or manually position or rotate the scanning device 100 for scanning the object. The scanning device 100 is configured to capture multiple angles and perspectives of the object. The 3D scanning system 10 includes the central processor 203 including integrated software to process, merge, and analyze data from the scanning device 100 and generate a 3D representation of the object. The scanning device 100 is configured for adjustment in height, curvature, and length based on a desired point of view and degree of freedom in a scanning process relative to the object.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. A system for 3D scanning and visualization for modelling an orthosis to a patient's limb, the system comprising:

a) a scanning device including a LiDAR camera and a TrueDepth camera, the scanning device configured to capture detailed depth information from the limb;

b) reality glasses configured to modify the appearance of the limb;

c) a charging console comprised of a station designed to provide power and replenish a battery;

d) a central processor including a software interface configured as a digital platform to process, analyze, and display data acquired by the scanning device, the central processor being in communication with the reality glasses, wherein the central processor includes an augmented reality environment in conjunction with artificial intelligence configured to provide real-time visual feedback, the visual feedback configured to predict limb deformation and suggest optimal positioning of the limb during a skeletal reduction procedure, the skeletal reduction procedure including at least one of setting a fracture of the limb and adjusting a bone of the limb, the visual feedback including visual aids within the augmented reality environment including initial and predicted X-ray images of the limb; and e) a handheld station supporting the scanning device, the handheld station configured to facilitate manipulation of the scanning device to acquire the data related to the limb.

2. The system of claim 1, wherein the reality glasses are comprised of at least one of augmented reality and virtual reality glasses.

3. The system of claim 1, wherein the software interface is further configured to allow users to select from different types of appendages and structural designs for the orthosis.

4. The system of claim 1, wherein the software interface is further configured to provide telehealth features, enabling a medical professional to remotely validate fitting of the brace or cast.

5. The system of claim 1, wherein the software interface is further configured to utilize a mix of data from the TrueDepth and LiDAR cameras for enhanced scanning accuracy and depth perception.

6. The system of claim 1, wherein the reality glasses are configured to display a real-time visualization of the limb, overlaid with a virtual representation of the orthosis.

7. The system of claim 1, wherein the software interface is further configured to provide interactive features for pediatric users, including how to use, animations, interactive avatars guiding the pediatric users through a scanning process, and interactive AI-assisted process/avatar to assure the limb is in a correct positioning.

8. The system of claim 1, wherein the software interface is further configured to display a position outline of the limb during a scanning process.

9. The system of claim 1, wherein the software interface is further configured to allow users to adjust a positioning of the limb post-scan using the artificial intelligence associated with the central processor.

10. The system of claim 1, wherein the software interface is further configured to enable a remote provider to join a scanning session and assist with positioning of the limb.

11. The system of claim 1, wherein the software interface is further configured to simulate the orthosis positioned on the limb in various scenarios, including sports practice and vocational requirements.

12. The system of claim 1, wherein the software interface is further configured to display medical images including at least one of X-rays, computerized tomography (CT), and magnetic resonance imaging (MRI) of the limb to assist visualization of one of a pathology, wound management, predicting possible inflammation, and confirmation of coverage of an injury.

13. The system of claim 1, wherein the scanning device includes a laser-assisted device, the laser-assisted device attached to a sensor to guide a scanning process, validate a required resolution, and provide convergence of focus when single or multiple lasers are used.

14. The system of claim 1, wherein the central processor includes an alternate reality environment including a virtual reality (VR) environment, the alternate reality environment configured to visually represent a stepwise design, the stepwise design configured to aid in determining a number of adjustments needed and facilitate modification of a design of the orthosis.

15. The system of claim 1, further comprising:

a 3D pointer in communication with the central processor, the 3D pointer configured to interact within the augmented reality environment and a virtual reality environment, the 3D pointer configured to identify areas of interest of the limb, the areas of interest including pain points, injuries, wounds, and other markers on the limb.

16. The system of claim 1, wherein the central processor is configured to determine a range of motion of the limb based on the data acquired by the scanning device, the system configured to set restrictions and exclusion angles for articulating devices of the orthosis, the limb comprised of an arm with an elbow and the system configured to restrict elbow flexion beyond a predetermined degree and limit the range of motion.

17. The system of claim 1, wherein the scanning device is in communication with a scanning software, the scanning software supports multi-user access, the multi-user access configured to allow multiple stakeholders to share an augmented reality space, the multiple stakeholders including clinicians, patients, and designers, the augmented reality space configured to allow the clinician to view the orthosis, the augmented reality space configured to facilitate simultaneous style and design adjustments of the orthosis, thereby ensuring a collaborative approach to treatment.

18. The system of claim 1, further comprising:

a mirror configured for real-time feedback, screen mirroring, and user visualization settings.

19. A system for scanning an object, the system comprising:

a mechanism for secure mounting of a scanning device equipped with a LIDAR sensor or a TrueDepth camera, the mechanism configurable to at least one of:

(a) allow the scanning device to traverse around the object, the scanning device configured to capture multiple angles and perspectives of the object and (b) manually position the scanning device for scanning; and a central processor including integrated software to process, merge, and analyze data from the scanning device and generate a 3D representation of the object, the central processor includes an augmented reality environment in conjunction with artificial intelligence configured to provide real-time visual feedback, the visual feedback configured to predict limb deformation and suggest optimal positioning of the limb during a skeletal reduction procedure, the skeletal reduction procedure including at least one of setting a fracture of the limb and adjusting a bone of the limb, the visual feedback including visual aids within the augmented reality environment including initial and predicted X-ray images of the limb.

20. The system of claim 19, wherein the scanning device is in communication with a scanning software and the augmented reality environment configured to validate fitting of an orthosis.

21. The system of claim 19, wherein the scanning device includes a laser-assisted device, the laser-assisted device attached to a sensor to guide a scanning process, validate a required resolution, and provide convergence of focus when single or multiple lasers are used.

22. The system of claim 19, further comprising:

a 3D pointer in communication with the central processor, the 3D pointer configured to interact within the augmented reality environment and a virtual reality environment, the 3D pointer configured to identify areas of interest of the limb, the areas of interest including pain points, injuries, wounds, and other markers on the limb.

23. The system of claim 19, wherein the central processor is configured to determine a range of motion of the limb based on the data from the scanning device, the system configured to set restrictions and exclusion angles for articulating devices of an orthosis, the limb comprised of an arm with an elbow and the system configured to restrict elbow flexion beyond a predetermined degree and limit the range of motion.

* * * * *